United States Patent [19]

Chen et al.

[11] Patent Number: 5,679,878
[45] Date of Patent: Oct. 21, 1997

[54] PROCESS FOR DEHYDROGENATION OF ALKYL AROMATIC COMPOUNDS

[75] Inventors: Shiou-Shan Chen, Winchester; Joseph C. Peters, Quincy, both of Mass.; Lionel C. Allmand, Baton Rouge, La.

[73] Assignee: Deltech Corporation, Whippany, N.J.

[21] Appl. No.: 967,517

[22] Filed: Oct. 28, 1992

[51] Int. Cl.$^6$ .............................. C07C 2/64; C07C 15/46
[52] U.S. Cl. .................... 585/444; 585/440; 585/435
[58] Field of Search ................................ 585/440, 444, 585/445, 435

[56] References Cited

U.S. PATENT DOCUMENTS

| | | | |
|---|---|---|---|
| 3,631,213 | 12/1971 | Brewer | 260/669 |
| 4,291,183 | 9/1981 | Crum et al. | 585/443 |
| 4,291,184 | 9/1981 | Crum et al. | 585/443 |
| 4,551,571 | 11/1985 | Sarumaru et al. | 585/440 |
| 4,590,324 | 5/1986 | Satek | 585/444 |
| 4,982,034 | 1/1991 | Moore et al. | 584/435 |

Primary Examiner—Glenn A. Caldarola
Assistant Examiner—P. Achutamurthy
Attorney, Agent, or Firm—Perman & Green, LLP

[57] ABSTRACT

This invention relates to a vapor phase process for the production of an alkyl styrene by the catalytic dehydrogenation of tertiary butylethylbenzene in the presence of catalysts containing iron oxides under conditions which minimize the undesirable thermal degradation of the raw material and the product while maintaining good yield and selectivity with low production of by-products. Specifically, it has been discovered that these desired results may be obtained by conducting the subject reaction at relatively low temperatures of between about 1000° F. and about 1100° F. and by maintaining a low partial pressure (i.e., not greater than about 0.5 psi) of the alkyl ethylbenzene in the reaction mixture. The desired partial pressure of the alkyl ethylbenzene is obtained by carrying out the catalytic reaction at a pressure of between about 1 psia and about 30 psia with steam as a diluent, the weight ratio of steam to alkyl ethylbenzene being between about 3 and about 30.

16 Claims, No Drawings

PROCESS FOR DEHYDROGENATION OF ALKYL AROMATIC COMPOUNDS

BACKGROUND OF THE INVENTION

1. Field of the Invention

This invention relates to a process for the production of alkylated styrenes, more particularly tertiarybutylstyrene, wherein the corresponding saturated alkyl aromatic compound is dehydrogenated in the vapor phase by contacting it with a suitable dehydrogenation catalyst at temperatures of less than 1100° F. and a partial pressure of said alkylaromatic compound of less than about 0.5 psi.

2. Description of Related Art

Para-tertiarybutylstyrene (PTBS) and para-methylstyrene (PMS) are known compounds which have varied uses. They may be used alone or in combination with styrene as a curing or crosslinking agent for unsaturated polyesters. They may be readily homopolymerized or copolymerized with monomers such as styrene, alpha methyl styrene, isoprene and 2-methyl-2-butene using Friedel Crafts catalysis to produce resins having improved clarity as well as resins useful in hot melt adhesive and paint applications. PMS may also be copolymerized with isobutylene to form functionalized copolymers which can be crosslinked or otherwise functionalized through the methyl styrene group.

These styrene compounds are generally produced by dehydrogenating or oxydehydrogenating the corresponding alkyl aromatic hydrocarbon in the vapor state over a suitable catalyst at elevated temperatures in accordance with the reaction scheme:

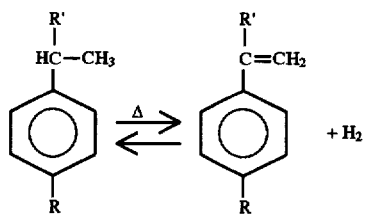

wherein R is $CH_3$ or $C(CH_3)_3$ and R' is hydrogen or $CH_3$. This reaction is reversible and the degree of conversion is determined by the equilibrium. Higher reaction temperatures therefore favor a higher degree of conversion.

However, conducting the dehydrogenation reaction at high temperatures, e.g. in excess of about 1100° F. can lead to certain problems. For example, when making an alkyl-substituted styrene from an alkyl-substituted ethylbenzene, a problem arises in regard to the alkyl substituent which may be dehydrogenated. As the number of carbon atoms in the alkyl group becomes greater, for example, dehydrogenating tertiary butyl ethylbenzene, this problem becomes more severe. Consequently, the selectivity to the desired product is low. Further, when tertiary butyl ethylbenzene is dehydrogenated, dialkenylbenzene impurities are produced. Because of the presence of two polymerizable unsaturated groups, a dialkenylbenzene such as isopropenylstyrene tends to undergo crosslinking activity and form insoluble by-products. Heat exchangers and distillation columns can be rendered inoperative. Further, the presence of an isopropenylstyrene type impurity in the tertiarybutylstyrene product can complicate or even prohibit the application of the product as a co-monomer in polymerizable formulations.

U.S. Pat. No. 3,631,213 discloses a process for the preparation of tertiarybutylstyrene (TBS) by the vapor phase catalytic dehydrogenation of t-butylethylbenzene (TBEB) over an iron oxide catalyst. Reactor temperatures ranging from 1075° to 1100° F. are employed and the reaction is conducted at pressures of 24 psig and above such that the partial pressure of TBEB in the system appears to be in excess of 0.5 psi. The disclosed yield of para-TBS is poor, generally less than 45% by weight based on the weight of para-TBEB starting material.

In addition, when TBEB is dehydrogenated in the vapor phase at high temperature, not only is the selectivity to TBS and para-TBS low, but the production of dialkenylbenzene is substantial.

Other processes for the dehydrogenation of alkyl aromatic compounds are disclosed in U.S. Pat. Nos. 4,113,787, 4,229,603 and 4,479,025.

Recent efforts by other researchers have been directed to oxydehydrogenation processes at lower temperatures, such as those described in U.S. Pat. Nos. 4,291,183, 4,291,184 and 4,982,034. However, oxydehydrogenation is carried out with oxygen as a reactant. It is inherently more hazardous than dehydrogenation. Further, oxydehydrogenation may also produce oxygenated organic compounds which even in minute quantities may significantly alter the properties of the tertiarybutylstyrene product. The invention which is the subject of this disclosure minimizes or eliminates the problems described above.

SUMMARY OF THE INVENTION

This invention relates to a vapor phase process for the production of an alkyl styrene by the catalytic dehydrogenation of tertiary butylethylbenzene in the presence of a catalyst containing iron oxides under conditions which minimize the undesirable thermal degradation of the raw material and the product while maintaining good yield and selectivity with low production of dialkenyl by-products. Specifically, it has been discovered that these desired results may be obtained by conducting the subject reaction at relatively low temperatures of between about 1000° F. and about 1100° F. and by maintaining a low partial pressure (i.e., not greater than about 0.5 psi) of the alkyl ethylbenzene in the reaction mixture. The desired partial pressure of the alkyl ethylbenzene is obtained by carrying out the catalytic reaction at a pressure of between about 1 psia and about 30 psia with steam as a diluent, the weight ratio of steam to alkyl ethylbenzene being between about 3 and about 30.

DETAILED DESCRIPTION OF THE INVENTION

The process of the present invention is generally applicable to the dehydrogenation of aromatic hydrocarbons having the structure:

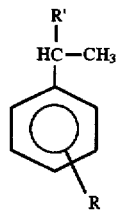

wherein R is $C(CH_3)_3$ and is located in the para or meta position on the aromatic ring, and R' is hydrogen or $CH_3$. Examples of suitable starting materials include para or meta tertiary butylethylbenzene and para or meta tertiary butylisopropyl benzene, as well as mixtures of these isomers. The process is particularly suited for the production of para-tertiary butylstyrene (para-TBS) using relatively pure para-tertiarybutylethylbenzene (para-TBEB) as a starting material because it offers particular advantages in terms of yield and reduction in the formation of undesirable by-products associated with the production of this material.

Accordingly, the invention will be further described with references to para-TBEB as the starting aromatic, although it is understood that the invention is equally applicable to the dialkyl aromatics described above as well as mixed isomers thereof.

In accordance with the process of this invention, a mixture of TBEB and superheated steam is introduced into a suitable reactor and contacted with one or more beds of dehydrogenation catalyst under dehydrogenation conditions which include a temperature in the range of from about 1,000° to 1100° F., more preferably from about 1015° to about 1075° F., at pressures ranging from subatmospheric to superatmospheric, i.e., from 1 to 30 psia, at a liquid hourly space velocity within the range of about 0.1 up to about 2.0 c.c. per c.c. of catalyst, preferably from 0.1 to 1.0, and wherein the weight ratio of steam to TBEB lies within the range of from about 3 to about 30 lbs of steam per pound of TBEB.

A key aspect to the effectiveness of the present process is that the partial pressure exerted on the system by TBEB be controlled such that it does not exceed about 0.5 psi and more preferably does not exceed about 0.25 psi and most preferably does not exceed about 0.15 psi. It has been found that control of TBEB partial pressures below these levels enhances selectively to the production of TBS and minimizes the formation of dialkenylbenzenes such as isopropenyl and butenyl styrenes, as discussed above. This control is achieved by selecting a steam to hydrocarbon ratio which is determined as a function of the total system pressure such that higher steam to hydrocarbon levels within the 3 to 30:1 ratio are utilized at higher system pressures and lower steam to hydrocarbon levels are utilized at lower system pressures. The exact amount of steam required in the process to achieve a desired TBEB partial pressure can be determined by the formula:

$$P_{TBEB} = TSP \times \frac{\text{Moles Tbeb}}{\text{Moles Tbeb} + \text{Moles H}_2\text{O}}$$

wherein $P_{TBEB}$ is the TBEB partial pressure and TSP is the total system pressure. Thus, for any given system pressure, the quantity of steam necessary to maintain the partial pressure of TBEB in the system below 0.5 can be calculated. In general, the process is most preferably conducted using a steam to TBEB weight ratio of from about 3 to about 10 to one where the dehydrogenation process is conducted at subatmospheric pressure and a ratio of from about 10 to about 30 to one where the process is conducted at above atmospheric pressure. The most preferred steam to TBEB weight ratios lie within the range of from about 5 to about 20 to one.

Operating within the above parameters, it has been found that good conversion ratios of TBEB to TBS in excess of 50%, or even in excess of 60%, can be achieved while at the same time levels of less than 20,000 ppm, preferably less than about 10,000 ppm, of dialkenylbenzene by-products are produced.

The para-TBEB which is fed to the dehydrogenation reactor is produced by alkylating ethyl benzene with isobutylene. A suitable process is described in U.S. Pat. No. 3,631,213 or in U.S. Pat. No. 4,469,908. The latter patent discloses a process wherein ethylbenzene is contacted with isobutylene in the presence of a ZSM-12 catalyst composition in a suitable reactor and under conditions of temperature and pressure such that alkylation takes place. The reactants are present at least partially in the liquid phase, preferably substantially totally in the liquid phase. These conditions include a reaction temperature within the range of from about 250° to 450° F., more preferably from about 300° to 400° F. and pressures ranging from about 100 to 1000 psig, depending upon reaction temperature. Preferred pressures range from 300 to 600 psig.

The reactor effluent generally comprises a mixture of excess unreacted ethylbenzene, the tertiary butylethylbenzene as well as other impurities. The ethylbenzene may be separated by distillation and recycled back to the alkylation reactor. The bottoms from the distillation column are then further distilled to separate the desired tertiary butyl ethylbenzene from other heavies.

The dehydrogenation reaction is conducted in the absence of added oxygen by preheating a mixture of steam and TBEB, optionally containing an inert gas such as nitrogen, to a temperature of up to 1100° F., introducing this mixture into a suitable reactor, and passing this mixture through one or more beds of dehydrogenation catalyst at a liquid hourly space velocity in the range of from about 0.1 to 2.0, more preferably from about 0.1 to 1.0 c.c. of TBEB per c.c. of catalyst, while maintaining an average reactant temperature of from about 1000° to 1100° F., more preferably from about 1015° to 1075° F.

Suitable dehydrogenation catalysts which may be employed are ferric oxide-based catalysts. Particularly preferred are catalysts comprising ferric oxide which also contain one or more different metal oxide promoters such as chromium oxide, and one or more oxides, hydroxides or salts of alkali or alkaline earth metals. Such catalysts may also include from about 0.01 to 2.5% of elemental platinum or palladium, and may include a support or binder such as silica or alumina. Suitable such catalysts and process for using them are disclosed in U.S. Pat. Nos. 3,631,213 and 4,113,787, the disclosures of which are incorporated herein by reference.

The product from the dehydrogenation is then subjected to one or more conventional vacuum distillation or evaporation steps to separate the tertiary butyl styrene from the non-dehydrogenated products. It is also desirable to include small amounts of a polymerization inhibitor which will retard the tendency of the monomer to partially polymerize as a consequence of the heat applied during distillation. Typical of such compounds are nitro-cresols such as disclosed in U.S. Pat. No. 4,182,658, mixed with the distillation material at levels within the range of about 50 to 3,000 ppm. Suitable distillation processes are disclosed in U.S. Pat. No. 4,469,558 and 4,376,678.

The following examples are illustrative of the invention.

EXAMPLES 1–18

A representative quantity of para tertiary ethyl benzene containing greater than 95% by weight of the para isomer was dehydrogenated by passing a mixture of it and steam through a 41" long, ½" diameter tubular pipe reactor packed with a 6" bed of pellets of a bound ferric oxide dehydrogenation catalyst marketed by United Catalysts Inc. of Louisville, Ky. under the designation G-64E.

The dehydrogenation reaction was conducted at various average temperatures, pressures, steam to TBEB weight ratios (SHR-wt) and space velocities (LHSV) as reported in Table 1. Table 1 also reports the TBS yields, conversion ratio, selectivity to para TBS, TBEB partial pressure and the weight of isopropenyl styrene impurity (IPS) produced under each operating condition.

An analysis of the data in Table 1 shows that with respect to Examples 1, 2, 7, 8 and 18 that there is insufficient water present in the reaction mixture at atmospheric or above atmospheric conditions to maintain the partial TBEB pressure below the

TABLE 1

| EX-AMPLE | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| Temp (°F.) | 1067 | 1067 | 1065 | 1063 | 1038 | 1017 | 1065 | 1065 | 1065 | 1035 | 1035 | 1035 | 1035 | 1035 | 1035 | 1035 | 1010 | 1065 |
| SHR (wt) | 5.2 | 5.4 | 4.9 | 7.9 | 7.8 | 7.8 | 5 | 5 | 15 | 15 | 15 | 15 | 20 | 15 | 20 | 20 | 20 | 5 |
| LHSV | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 |
| PRESS | 0 | 0 | 6* | 6* | 6* | 6* | 0 | 0 | 7 | 7 | 15 | 7 | 7 | 7 | 7 | 7 | 7 | 0 |
| P-TBEB conv. % | 57.5 | 56.5 | 62.8 | 65.3 | 53.8 | 43.8 | 60.5 | 58.8 | 56.4 | 43.9 | 42.8 | 44.0 | 41.4 | 43.3 | 41.2 | 56.8 | 43.8 | 61.3 |
| Sel to P-TBS % | 78.9 | 85.8 | 90.6 | 91.6 | 93.3 | 94.2 | 87.4 | 82.6 | 90.7 | 92.8 | 91.4 | 93.1 | 91.4 | 90.5 | 89.2 | 87.5 | 89.2 | 89.4 |
| Yield P-TBS % | 45.4 | 48.5 | 56.9 | 59.8 | 50.2 | 41.2 | 52.9 | 48.5 | 51.1 | 40.7 | 39.1 | 41.0 | 37.8 | 39.2 | 36.7 | 49.7 | 39.1 | 51.7 |
| P-TBEB Partial Pressure (psi) | 0.31 | 0.31 | 0.10 | 0.07 | 0.07 | 0.07 | 0.31 | 0.46 | 0.15 | 0.15 | 0.21 | 0.15 | 0.11 | 0.15 | 0.11 | 0.11 | 0.11 | 0.31 |
| IPS By-Product (ppm × $10^{31\ 3}$ rel. to P-TBS) | 20.0 | 12.8 | 6.4 | 4.4 | 2.5 | 1.6 | 11.9 | 17.9 | 5.0 | 2.9 | 3.3 | 2.8 | 2.4 | 3.8 | 2.9 | 5.5 | 3.2 | 12.7 |

*Pressure value is psia. Pressure otherwise psig unless noted differently.

preferred 0.25 psi level. Accordingly, relatively high concentrations above 10,000 ppm relative to P-TBS of isopropenyl styrene are produced. Increasing the steam to hydrocarbon ratio SHR under the subatmospheric conditions produced good conversion rates for P-TBEB and higher yields and selectivity towards P-TBS. A comparison of Examples 9-17 with Examples 1, 2, 7, 8 and 18 shows that a considerably higher steam to hydrocarbon ratio is required at above atmospheric presure operating conditions to maintain the levels of isopropenyl styrene below about 10,000 ppm.

What is claimed is:

1. A process for dehydrogenating an alkylaromatic hydrocarbon having the formula:

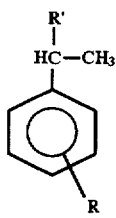

wherein R is C(CH$_3$)$_3$ located in the para or meta position on the aromatic ring and R' is hydrogen or CH$_3$, comprising contacting a mixture comprising steam and said aromatic hydrocarbon in the absence of added oxygen with a dehydrogenation catalyst at an average temperature in the range of from about 1000° F. to below about 1100° F. the weight ratio of steam to said aromatic hydrocarbon being in the range of from about 3:1 to about 30:1, respectively, such that the partial pressure exerted by said aromatic hydrocarbon in the system is less than about 0.25 psi, and recovering an effluent comprising a dehydrogenated aromatic hydrocarbon.

2. The process of claim 1 which is conducted at a pressure within the range of from 1 to about 30 psia.

3. The process of claim 2 wherein said process is conducted at a liquid hourly space velocity in the range of from about 0.1 to about 2.0.

4. The process of claim 1 wherein said aromatic hydrocarbon is para-tertiary butylethylbenzene and said effluent comprises para-tertiarybutylstyrene.

5. The process of claim 4 which is conducted at a pressure within the range of from 1 to about 30 psia.

6. The process of claim 4 wherein said process is conducted at a liquid hourly space velocity in the range of from about 0.1 to about 2.0.

7. The process of claim 4 wherein said recovered effluent contains less than about 20,000 ppm of isopropenyl styrene based on the weight of said para-tertiary butylstyrene produced.

8. The process of claim 7 wherein said recovered effluent contains less than about 10,000 ppm of isopropenyl styrene based on the weight of said para-tertiary butylstyrene.

9. The process of claim 4 which is conducted at atmospheric or subatmospheric pressure and the amount of steam mixed with said para-tertiary butylethylbenzene is less than about 10 to 1 by weight.

10. The process of claim 9 wherein said steam is present at a weight ratio of from about 5:1 to 10:1, respectively.

11. The process of claim 4 which is conducted at above atmospheric pressure and the amount of steam mixed with said para-tertiary butylethylbenzene is greater than about 10 to 1 by weight.

12. The process of claim 11 wherein said steam is present at a weight ratio of from about 10:1 to 20:1, respectively.

13. The process of claim 1 wherein the partial pressure of said aromatic hydrocarbon is less than about 0.15 psi.

14. The process of claim 9 which is conducted at subatmospheric pressure.

15. The process of claim 14 wherein the steam is present at a weight ratio of from about 3:1 to about 10:1, respectively.

16. The process of claim 1 wherein said catalyst comprises ferric oxide.

* * * * *